United States Patent
Song et al.

(10) Patent No.: US 9,540,331 B2
(45) Date of Patent: Jan. 10, 2017

(54) PREPARATION METHOD OF DEXMEDETOMIDINE INTERMEDIATE

(71) Applicant: TIANJIN WEIJIE PHARMACEUTICAL CO., LTD, Tianjin (CN)

(72) Inventors: Honghai Song, Tianjin (CN); Zhicun Sun, Tianjin (CN); Haiping Huang, Tianjin (CN); Chao Zhang, Tianjin (CN)

(73) Assignee: TIANJIN WEIJIE PHARMACEUTICAL CO., LTD (CN)

( * ) Notice: Subject to any disclaimer, the term of this patent is extended or adjusted under 35 U.S.C. 154(b) by 0 days.

(21) Appl. No.: 15/033,777

(22) PCT Filed: Oct. 9, 2014

(86) PCT No.: PCT/CN2014/088182
§ 371 (c)(1),
(2) Date: May 2, 2016

(87) PCT Pub. No.: WO2015/078235
PCT Pub. Date: Jun. 4, 2015

(65) Prior Publication Data
US 2016/0272594 A1    Sep. 22, 2016

(30) Foreign Application Priority Data
Nov. 27, 2013    (CN) .......................... 2013 1 0624927

(51) Int. Cl.
C07D 491/107    (2006.01)
C07D 487/10     (2006.01)
C07D 487/04     (2006.01)
C07D 491/06     (2006.01)
C07D 471/04     (2006.01)
C07D 498/08     (2006.01)
C07D 471/10     (2006.01)
C07D 495/10     (2006.01)
C07D 233/90     (2006.01)

(52) U.S. Cl.
CPC ................... C07D 233/90 (2013.01)

(58) Field of Classification Search
CPC .................................................. C07D 233/64
See application file for complete search history.

(56) References Cited

FOREIGN PATENT DOCUMENTS

| CN | 101535272 | | 9/2009 |
|---|---|---|---|
| CN | 101805294 | | 8/2010 |
| CN | 101921234 | | 12/2010 |
| CN | 101921234 A | * | 12/2010 |
| CN | 102452984 | | 5/2012 |
| CN | 102753532 | | 10/2012 |
| EP | 1918282 | | 5/2008 |
| WO | 2013014428 | | 1/2013 |

OTHER PUBLICATIONS

Graphical Synthetic Routes of Dexmedetomidien Hydrochloride; Chinese Journal of Pharmaceuticals vol. 39, No. 6, Jun. 10, 2008; pp. 467-469.
Office Action dated Nov. 4, 2014 from corresponding No. CN 201310624927.8 with English translation.
International Search Report dated Jan. 19, 2015 from corresponding No. PCT/CN2014/088182.
Notification of Authorization dated Feb. 17, 2015 from corresponding No. CN 201310624927.8.

* cited by examiner

*Primary Examiner* — Nyeemah A Grazier
*Assistant Examiner* — Amanda L Aguirre
(74) *Attorney, Agent, or Firm* — Hauptman Ham, LLP

(57) ABSTRACT

The present invention discloses a preparation method of 2,3-dimethyl phenyl-1-trityl-imidazole-4-ketone. In accordance with this method, imidazole-4-ethyl formate is used as a raw material; ethyl formate is used for amino protection, 1-trityl-1H-imidazole-4-formic acid is obtained after basic hydrolysis; 1-trityl-1H-imidazole-4-formic acid and N,O-dimethylhydroxylamine hydrochloride are subjected to condensation so as to obtain N-methoxyl-N-methyl-1-trityl-1H-imidazole-4-formamide; and N-methoxyl-N-methyl-1-trityl-1H-imidazole-4-formamide and a Grignard reagent prepared by the reaction of 2,3-dimethylbromobenzene with magnesium are subjected to a Grignard reaction, and then the target product 2,3-dimethyl phenyl-1-trityl-1H-imidazole-4-ketone is obtained. Compared with the reported preparation methods, the preparation method is more convenient to operate and is beneficial for industrial production.

6 Claims, No Drawings

PREPARATION METHOD OF DEXMEDETOMIDINE INTERMEDIATE

TECHNICAL FIELD

The present invention belongs to the technical field of medicines, in particular to a preparation method of dexmedetomidine intermediate, 2,3-dimethyl phenyl-1-trityl-imidazole-4-ketone.

BACKGROUND

Medetomidine is a racemic mixture of two optical enantiomers, which namely levmedetomidine (LEV) and dexmedetomidine (DEX), at an equal ratio (MacDonald et al., 1991; Savola and Virtanen, 1991). Such compound has high selectivity on 2-epinephrine acceptor, and is a novel alpha2-receptor stimulant with 4-replaced imidazole ring (Savola et al, 1986).

At present, there are several known methods for preparing the medetomidine.

Kudzma et al. put forward a multi-step method for preparing the medetomidine. This method has disadvantages of using compounds with high flammability and high corrosion, such as butyl lithium, and of reacting at a low temperature of about −78° C.

The European patent EP1918282 discloses a preparation method of medetomidine and its salt. According to the method, the transmetalation of the halogenated imidazole is carried out by using the Grignard reagent, and then imidazole reacts with 2,3-dimethylbezaldehyde to generate alcohol, and the alcohol is oxidized by using manganese dioxide to generate 2,3-dimethyl phenyl-1-trityl-imidazole-4-ketone. The method is disadvantaged in using trityl chloride to perform nitrogen protection and deprotection on imidazole, so the operation process is complicated.

Cordi et al. disclose a preparation method of medetomidine in tartrate form. This method has the disadvantage that the raw material is very expensive.

GB 2453982 discloses a preparation method of medetomidine, including reaction between 2,3-dimethyl-methylbenzyl alcohol and N-trimethylsilylimidazole. The method is disadvantaged in using strong Lewis acid and excessive reagents.

SUMMARY

To solve the above problems, the objective of the present invention is to provide a preparation method of dexmedetomidine intermediate, 2,3-dimethyl phenyl-1-trityl-imidazole-4-ketone which is high in yield, low in cost, simple to operate, good in safety, environmentally-friendly and suitable for industrial production.

To fulfill the above objective, the preparation method of the dexmedetomidine intermediate, 2,3-dimethyl phenyl-1-trityl-imidazole-4-ketone, includes the following steps:

1) taking triethylamine as an alkaline protonation reagent, performing amino protection on imidazole-4-ethyl formate by using triphenylchloromethane to generate 1-trityl-1H-imidazole-4-ethyl formate;

2) hydrolyzing 1-trityl-1H-imidazole-4-ethyl formate in alkaline liquor, then performing acid precipitation to obtain 1-trityl-1H-imidazole-4-formic acid;

3) with the existence of a condensation reagent and under alkaline conditions, performing condensation on 1-trityl-1H-imidazole-4-formic acid and N,O-dimethylhydroxylamine hydrochloride to generate N-methoxyl-N-methyl-1-trityl-1H-imidazole-4-formamide;

4) preparing Grignard reagent, 2,3-dimethyl phenyl magnesium halide, through reaction between 2,3-dimethylhalobenzene and magnesium;

5) performing Grignard reaction between N-methoxyl-N-methyl-1-trityl-1H-imidazole-4-formamide and 2,3-dimethyl phenyl magnesium halide to generate 2,3-dimethyl phenyl-1-trityl-1H-imidazole-4-ketone.

The synthesis route is as follows:

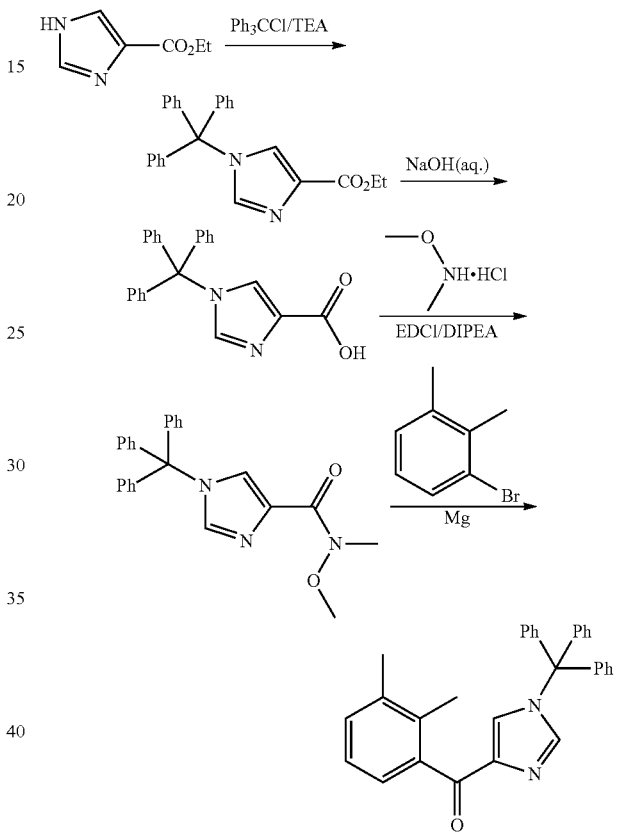

In step 1), the mole ratio of imidazole-4-ethyl formate and triphenylchloromethane is 1:1.0~1.5, while the mole ratio of the triethylamine to the triphenylchloromethane is 1.0~1.5:1.

In step 2), the alkaline is selected from at least one of potassium hydroxide, sodium hydroxide, sodium carbonate and potassium carbonate; the concentration of alkaline liquor is 1.0~3.0 M, 3~10 equivalent.

In step 3), the condensation reagent is 1-ethyl-3-(3-dimethylamino propyl)carbodiimide hydrochloride (EDCI); the alkaline is selected from trimethylamine, triethylamine, N,N-diisopropylethylamine (DIEPA) and tributylamine; the mole ratio of 1-ethyl-3-(3-dimethylamino propyl) carbodiimide hydrochloride to 1-trityl-1H-imidazole-4-formic acid is 1.0~1.5, and the mole ratio of alkaline to 1-trityl-1H-imidazole-4-formic acid is 2.0~4.0.

In step 4), 2,3-dimethylhalobenzene is 2,3-dimethylchlorobenzene, 2,3-dimethylbromobenzene or 2,3-dimethyliodobenzene.

In step 5), Grignard reaction temperature is −10-25° C.

The total yield by using the preparation method of the present invention is 51%, and the raw materials used during the reaction, for example, triphenylchloromethane, EDCI, 2-3-dimethylhalobenzene, are low in price and easily obtained. In the former three steps, the reactions proceed at room temperature, and in the fourth step the reaction is the Grignard reaction. During the reactions, only simple operations such as extraction, suction filtration and distillation are employed, which are very common in general production. No gas is generated during the reactions; no heat dissipation appears during post-processing; the operation is simple and the safety is high. Organic reaction solvents, such as dichloromethane, methanol, tetrahydrofuran, can be recycled; little waste water is generated during the post-processing, and water without effect on the environment can be obtained through the neutralization reaction, so the preparation method is applicable to industrial production.

DETAILED DESCRIPTION

The preparation method of the dexmedetomidine intermediate, 2,3-dimethyl phenyl-1-trityl-imidazole-4-ketone provided by the present invention is described in detail below.

Example 1

Add 100 g (0.714 mol, 1.0 eq) of imidazole-4-ethyl formate and 1.4 L of dichloromethane to a 2 L four-mouth bottle equipped with a mechanical stirring and a thermometer to form a suspension; add 219 g (0.787 mol, 1.1 eq) of triphenylchloromethane and 79.4 g (0.787 mol, 1.1 eq) of triethylamine to the suspension, slowly heat to 25~30° C., the liquid turns clear. Continue to stir for 20 h to the reaction finish. Add 200 mL water and stir 30 mins, then standing for layered. Separate the organic phase and extract the water phase by 100 mL dichloromethane. Combine the organic phase and wash it once by 200 mL water. Concentrate the organic phase to get alight yellow oil; then 500 mL diethyl ether is added, a great amount of white solids are generated when the mixed solution is stirred; filter and dry to obtain 269 g 1-trityl-1H-imidazole-4-ethyl formate, with a yield of 98% and a purity of 90% (HPLC).

Add 600 mL Methanol and 650 ml tetrahydrofuran to a 5 L dried four-mouth bottle equipped with a mechanical stirring and a thermometer, then add 125 g (0.327 mol, 1.0 eq) 1-trityl-1H-imidazole-4-ethyl formate; stir to form a suspension; 1 L sodium hydroxide solution (2M, 6 eq) is dropped into the suspension, wherein the temperature is controlled to be 10~20° C. Stir for 5 hrs and then the reaction ends. 1 L Hydrochloric acid solution (2M) is slowly dropped and a great amount of white solids are generated when the mixed solution is stirred. Adjust pH value to 5~6. Filter and dry to obtain 112 g 1-trityl-1H-imidazole-4-formic acid, with a yield of 96% and a purity of 97% (HPLC).

Add 112 g (0.316 mol, 1.0 eq) 1-trityl-1H-imidazole-4-formic acid and 784 mL dichloromethane as solvent to a 3 L four-mouth bottle equipped with a mechanical stirring and a thermometer, stir to form a suspension. 68.4 g (0.38 mol, 1.2 eq) EDCI, 137 g (1.06 mol, 3.3 eq) N,N-Ethyldiisopropylamine and 34.2 g (0.35 mol, 1.1 eq) N,O-dimethylhydroxylamine hydrochloride are added, with the temperature controlled to be 25~30° C.; the reaction lasts for 48 hrs and then ends. Add 100 mL water and stir for 30 mins, then standing for layered. Wash the organic phase by 240 mL hydrochloric acid (1M) until pH value is 6~7. Concentrate the organic phase and obtain 133 g crude N-methoxyl-N-methyl-1-trityl-1H-imidazole-4-formamide which is a colorless oil, with a yield of 100% and a purity of 70% (HPLC).

Add 17 g (0.69 mol, 2 eq) magnesium rod and 400 mL anhydrous THF as solvent to a 3 L dry four-mouth bottle equipped with a mechanical stirring, a thermometer and a constant-pressure dropping funnel. 13.3 g (0.072 mol, 0.21 eq) 2,3-dimethylbromobenzene is dissolved in 55 mL tetrahydrofuran and then mixture is added into the system; heating to initiate the reaction. Dissolve the residual 108.7 g (0.587 mol, 1.76 eq) 2,3-dimethylbromobenzene into 278 mL tetrahydrofuran and then drop into the system. Reflux 2 hrs, and then stop heating. Cool to −5° C., drop 200 mL tetrahydrofuran solution of 133 g (0.334 mol, 1.0 eq) N-methoxyl-N-methyl-1-trityl-1H-imidazole-4-formamide while the inner temperature is controlled to not exceed 25° C. After the dropping is complete, continue to stir for 12 hrs at room temperature, and then reaction ends. Add 50 g ammonium chloride which is dissolved in 150 mL water to quenching the reaction, while controlling the inner temperature not exceeds 15° C. After dropping is complete, add 500 mL dichloromethane, stir for 1 hr at 10~20° C. Filter to remove insoluble substances. The filtrate is separated into layers. Collect the organic phases, extract the water phase by 3×100 mL dichloromethane. Combine the organic phases and wash it by 2×100 mL water. Concentrate the organic phase, the residue is recrystallized in the solvents of 200 mL dichloromethane and 800 mL n-hexane. Obtain 80 g 2,3-dimethyl phenyl-1-trityl-1H-imidazole-4-ketone which is a light yellow solid, with a yield of 54% and a purity of 84% (HPLC).

Example 2

Add 100 g (0.714 mol, 1.0 eq) of imidazole-4-ethyl formate and 1.4 L of dichloromethane to a 2 L four-mouth bottle equipped with a mechanical stirring and a thermometer to form a suspension; add 259 g (0.93 mol, 1.3 eq) of triphenylchloromethane and 93.8 g (0.93 mol, 1.3 eq) of triethylamine to the suspension, slowly heat to 25~30° C., the liquid turns clear. Continue to stir for 20 h to the reaction finish. Add 200 mL water and stir 30 mins, then standing for layered. Separate the organic phase and extract the water phase by 100 mL dichloromethane. Combine the organic phase and wash it once by 200 mL water. Concentrate the organic phase to get alight yellow oil; then 500 mL diethyl ether is added, a great amount of white solids are generated when the mixed solution is stirred; filter and dry to obtain 265 g 1-trityl-1H-imidazole-4-ethyl formate, with a yield of 97% and a purity of 92% (HPLC).

Add 600 mL Methanol and 650 ml tetrahydrofuran to a 5 L dried four-mouth bottle equipped with a mechanical stirring and a thermometer, then add 125 g (0.327 mol, 1.0 eq) 1-trityl-1H-imidazole-4-ethyl formate; stir to form a suspension; 1 L potassium hydroxide solution (3M, 9 eq) is dropped into the suspension, wherein the temperature is controlled to be 10~20° C. Stir for 4 hrs and then the reaction ends. 1.5 L Hydrochloric acid solution (2M) is slowly dropped and a great amount of white solids are generated when the mixed solution is stirred. Adjust pH value to 5~6. Filter and dry to obtain 115 g 1-trityl-1H-imidazole-4-formic acid, with a yield of 98% and a purity of 96% (HPLC).

Add 112 g (0.316 mol, 1.0 eq) 1-trityl-1H-imidazole-4-formic acid and 784 mL dichloromethane as solvent to a 3 L four-mouth bottle equipped with a mechanical stirring and a thermometer, stir to form a suspension. 85.5 g (0.48 mol, 1.5 eq) EDCI, 129.5 g (1.28 mol, 4.0 eq) triethylamine and 40.4 g (0.41 mol, 1.3 eq) N,O-dimethylhydroxylamine hydrochloride are added, with the temperature controlled to be 25~30° C.; the reaction lasts for 48 hrs and then ends. Add 100 mL water and stir for 30 mins, then standing for layered. Wash the organic phase by 280 mL hydrochloric acid (1M) until pH value is 6~7. Concentrate the organic phase and obtain 135 g crude N-methoxyl-N-methyl-1-trityl-1H-imidazole-4-formamide which is a color-less oil, with a yield of 100% and a purity of 72% (HPLC).

Add 25 g (1.04 mol, 3 eq) magnesium rod and 400 mL anhydrous THF as solvent to a 3 L dry four-mouth bottle equipped with a mechanical stirring, a thermometer and a constant-pressure dropping funnel. 15.2 g (0.108 mol, 0.32 eq) 2,3-dimethylchlorobenzene is dissolved in 55 mL tetrahydrofuran and then mixture is added into the system; heating to initiate the reaction. Dissolve the residual 123.8 g (0.881 mol, 2.64 eq) 2,3-dimethylchlorobenzene into 278 mL tetrahydrofuran and then drop into the system. Reflux 2 hrs, and then stop heating. Cool to −5° C., drop 200 mL tetrahydrofuran solution of 133 g (0.334 mol, 1.0 eq) N-methoxyl-N-methyl-1-trityl-1H-imidazole-4-formamide while the inner temperature is controlled to not exceed 25° C. After the dropping is complete, continue to stir for 12 hrs at room temperature, and then reaction ends. Add 50 g ammonium chloride which is dissolved in 150 mL water to quench the reaction, while controlling the inner temperature not exceeds 15° C. After dropping is complete, add 500 mL dichloromethane, stir for 1 hr at 10~20° C. Filter to remove insoluble substances. The filtrate is separated into layers. Collect the organic phases, extract the water phase by 3×100 mL dichloromethane. Combine the organic phases and wash it by 2×100 mL water. Concentrate the organic phase, the residue is recrystallized in the solvents of 200 mL dichloromethane and 800 mL n-hexane. Obtain 110 g 2,3-dimethyl phenyl-1-trityl-1H-imidazole-4-ketone which is a light yellow solid, with a yield of 74% and a purity of 92% (HPLC).

Example 3

Add 100 g (0.714 mol, 1.0 eq) of imidazole-4-ethyl formate and 1.4 L of dichloromethane to a 2 L four-mouth bottle equipped with a mechanical stirring and a thermometer to form a suspension; add 259 g (0.93 mol, 1.3 eq) of triphenylchloromethane and 93.8 g (0.93 mol, 1.3 eq) of triethylamine to the suspension, slowly heat to 25~30° C., the liquid turns clear. Continue to stir for 20 h to the reaction finish. Add 200 mL water and stir 30 mins, then standing for layered. Separate the organic phase and extract the water phase by 100 mL dichloromethane. Combine the organic phase and wash it once by 200 mL water. Concentrate the organic phase to get alight yellow oil; then 500 mL diethyl ether is added, a great amount of white solids are generated when the mixed solution is stirred; filter and dry to obtain 265 g 1-trityl-1H-imidazole-4-ethyl formate, with a yield of 97% and a purity of 92% (HPLC).

Add 600 mL Methanol and 650 ml tetrahydrofuran to a 5 L dried four-mouth bottle equipped with a mechanical stirring and a thermometer, then add 125 g (0.327 mol, 1.0 eq) 1-trityl-1H-imidazole-4-ethyl formate; stir to form a suspension; 1 L sodium carbonate solution (3M, 9 eq) is dropped into the suspension, wherein the temperature is controlled to be 10~20° C. Stir for 4 hrs and then the reaction ends. 1.5 L Hydrochloric acid solution (2M) is slowly dropped and a great amount of white solids are generated when the mixed solution is stirred. Adjust pH value to 5~6. Filter and dry to obtain 115 g 1-trityl-1H-imidazole-4-formic acid, with a yield of 98% and a purity of 96% (HPLC).

Add 112 g (0.316 mol, 1.0 eq) 1-trityl-1H-imidazole-4-formic acid and 784 mL dichloromethane as solvent to a 3 L four-mouth bottle equipped with a mechanical stirring and a thermometer, stir to form a suspension. 85.5 g (0.48 mol, 1.5 eq) EDCI, 237 g (1.28 mol, 4.0 eq) tributylamine and 40.4 g (0.41 mol, 1.3 eq) N,O-dimethylhydroxylamine hydrochloride are added, with the temperature controlled to be 25~30° C.; the reaction lasts for 48 hrs and then ends. Add 100 mL water and stir for 30 mins, then standing for layered. Wash the organic phase by 280 mL hydrochloric acid (1M) until pH value is 6~7. Concentrate the organic phase and obtain 135 g crude N-methoxyl-N-methyl-1-trityl-1H-imidazole-4-formamide which is a color-less oil, with a yield of 100% and a purity of 72% (HPLC).

Add 25 g (1.04 mol, 3 eq) magnesium rod and 400 mL anhydrous THF as solvent to a 3 L dry four-mouth bottle equipped with a mechanical stirring, a thermometer and a constant-pressure dropping funnel. 25 g (0.108 mol, 0.32 eq) 2,3-dimethyliodobenzene is dissolved in 55 mL tetrahydrofuran and then mixture is added into the system; heating to initiate the reaction. Dissolve the residual 204.5 g (0.881 mol, 2.64 eq) 2,3-dimethyliodobenzene into 278 mL tetrahydrofuran and then drop into the system. Reflux 2 hrs, and then stop heating. Cool to −5° C., drop 200 mL tetrahydrofuran solution of 133 g (0.334 mol, 1.0 eq) N-methoxyl-N-methyl-1-trityl-1H-imidazole-4-formamide while the inner temperature is controlled to not exceed 25° C. After the dropping is complete, continue to stir for 12 hrs at room temperature, and then reaction ends. Add 50 g ammonium chloride which is dissolved in 150 mL water to quenching the reaction, while controlling the inner temperature not exceeds 15° C. After dropping is complete, add 500 mL dichloromethane, stir for 1 hr at 10~20° C. Filter to remove insoluble substances. The filtrate is separated into layers. Collect the organic phases, extract the water phase by 3×100 mL dichloromethane. Combine the organic phases and wash it by 2×100 mL water. Concentrate the organic phase, the residue is recrystallized in the solvents of 200 mL dichloromethane and 800 mL n-hexane. Obtain 126 g 2,3-dimethyl phenyl-1-trityl-1H-imidazole-4-ketone which is a light yellow solid, with a yield of 85% and a purity of 94% (HPLC).

What is claimed is:

1. A preparation method of dexmedetomidine intermediate 2,3-dimethylphenyl-1-trityl-1H-imidazole-4-ketone, characterized in that, said preparation method comprises the following steps in turn:
    1) taking triethylamine as an alkaline protonation reagent, performing amino protection on imidazole-4-ethyl formate by using triphenylchloromethane to generate 1-trityl-1H-imidazole-4-ethyl formate;
    2) hydrolyzing 1-trityl-1H-imidazole-4-ethyl formate in alkaline liquor, then performing acid precipitation to obtain 1-trityl-1H-imidazole-4-formic acid;
    3) with the existence of a condensation reagent and under alkaline conditions, performing condensation on 1-trityl-1H-imidazole-4-formic acid and N,O-dimethylhydroxylamine hydrochloride to generate N-methoxyl-N-methyl-1-trityl-1H-imidazole-4-formamide;
    4) preparing Grignard reagent, 2,3-dimethyl phenyl magnesium halide, through reaction between 2,3-dimethylhalobenzene and magnesium;
    5) performing Grignard reaction between N-methoxyl-N-methyl-1-trityl-1H-imidazole-4-formamide and 2,3-dimethyl phenyl magnesium halide to generate 2,3-dimethyl phenyl-1-trityl-1H-imidazole-4-ketone.

2. The preparation method according to claim 1, characterized in that, in step 1), the mole ratio of the imidazole- 4-ethyl formate and triphenylchloromethane is 1:1.0~1.5, while the mole ratio of triethylamine to triphenylchloromethane is 1.0~1.5:1.

3. The preparation method according to claim 1, characterized in that, in step 2), the alkaline is selected from at least one of potassium hydroxide, sodium hydroxide, sodium carbonate and potassium carbonate; the concentration of the alkaline liquor is 1.0~3.0 M, and the number of equivalents of alkaline liquor is 3-10.

4. The preparation method according to claim 1, characterized in that, in step 3), the condensation reagent is 1-ethyl-3-(3-dimethylaminopropyl)carbodiimide hydrochloride; the alkaline is selected from trimethylamine, triethylamine, N,N-diisopropylethylamine (DIEPA) and tributylamine; the mole ratio of 1-ethyl-3-(3-dimethylaminopropyl)carbodiimide hydrochloride to 1-trityl-1H-imidazole-4-formic acid is 1.0~1.5:1; and the mole ratio of alkaline to 1-trityl-1H-imidazole-4-formic acid is 2.0~4.0:1.

5. The preparation method according to claim 1, characterized in that, in step 4), the 2,3-dimethylhalobenzene is 2,3-dimethylchlorobenzene, 2,3-dimethylbromobenzene or 2,3-dimethyliodobenzene.

6. The preparation method according to claim 1, characterized in that, in step 5), Grignard reaction temperature is −10~25° C.

* * * * *